(12) United States Patent
Varlemann et al.

(10) Patent No.: US 6,429,235 B1
(45) Date of Patent: Aug. 6, 2002

(54) ENERGY-CURABLE COMPOSITION FOR MAKING A PRESSURE SENSITIVE ADHESIVE

(75) Inventors: Ulrike Varlemann, Randolph, MA (US); Ning Chen, Jamison, PA (US); Arifin Marzuki, Chester, PA (US); Ramesh Narayan, Horsham, PA (US)

(73) Assignee: Cognis Corporation, Gulph Mills, PA (US)

( * ) Notice: Subject to any disclaimer, the term of this patent is extended or adjusted under 35 U.S.C. 154(b) by 0 days.

(21) Appl. No.: 09/396,907

(22) Filed: Sep. 15, 1999

(Under 37 CFR 1.47)

Related U.S. Application Data

(60) Provisional application No. 60/151,039, filed on Aug. 27, 1999.

(51) Int. Cl.$^7$ .............................. C08F 2/50; C09J 4/02; C09J 175/16
(52) U.S. Cl. .......................... 522/14; 522/16; 522/37; 522/42; 522/44; 522/46; 522/50; 522/53; 522/93; 522/95; 522/96; 522/120; 522/121; 522/141; 522/142; 526/328; 526/328.5; 526/322
(58) Field of Search ............................ 522/42, 96, 95, 522/120, 141, 182, 183, 37, 44, 46, 50, 53, 14, 16, 93; 526/328, 328.5, 322

(56) References Cited

U.S. PATENT DOCUMENTS

| | | |
|---|---|---|
| 3,770,491 A | 11/1973 | Spoor et al. |
| 4,611,087 A | 9/1986 | Yamashita et al. |
| 4,642,126 A | 2/1987 | Zador et al. |
| 4,652,274 A | 3/1987 | Boettcher et al. |
| 4,714,655 A | 12/1987 | Bordoloi et al. |
| 4,847,329 A | 7/1989 | Koleske et al. |
| 5,104,921 A | 4/1992 | Erickson et al. |
| 5,115,025 A | 5/1992 | Koleske et al. |
| 5,179,183 A | 1/1993 | Koleske et al. |
| 5,212,210 A | 5/1993 | Halm |
| 5,391,602 A | 2/1995 | Skoultchi |
| 5,461,087 A | 10/1995 | Takahashi et al. |
| 5,489,624 A | 2/1996 | Kantner et al. |
| 5,512,612 A | 4/1996 | Brown et al. |
| 5,527,578 A | 6/1996 | Mazurek et al. |
| 5,536,768 A | 7/1996 | Kantner et al. |
| 5,641,567 A | 6/1997 | Brown et al. |
| 5,660,178 A | 8/1997 | Kantner et al. |
| 5,670,557 A | 9/1997 | Dietz et al. |
| 5,686,504 A | 11/1997 | Ang |
| 5,853,750 A | 12/1998 | Dietz et al. |
| 5,879,759 A | 3/1999 | Zang |
| 5,883,147 A | 3/1999 | Masuhara et al. |
| 5,900,473 A | 5/1999 | Acevedo et al. |
| 5,912,381 A | 6/1999 | Narayan et al. |

*Primary Examiner*—Susan W. Berman
(74) *Attorney, Agent, or Firm*—John E. Drach

(57) ABSTRACT

An energy-curable polymer-forming composition for making a pressure sensitive adhesive includes an unsaturated oligomer resin and an adhesive promoter which increases the peel strength of the adhesive without reducing its tack. The composition also includes a tackifier and various other optional components such as photoinitiator, chain extender, reactive diluent and the like.

19 Claims, No Drawings

ENERGY-CURABLE COMPOSITION FOR MAKING A PRESSURE SENSITIVE ADHESIVE

CROSS REFERENCE TO RELATED APPLICATIONS

This application claims priority to U.S. Provisional Application Serial No. 60/151,039, filed on Aug. 27, 1999.

BACKGROUND OF THE INVENTION

1. Field of the Invention

The present disclosure relates to adhesives, and particularly to pressure sensitive adhesives derived from energy-curable polymer-forming compositions.

2. Background of the Related Art

Pressure sensitive adhesives are known in the art. A pressure sensitive adhesive ("PSA") is one which in dry form is aggressively and permanently tacky at room temperature and which firmly adheres to a variety of dissimilar surfaces upon mere contact without the need of more than finger or hand pressure. PSA requires no activation by heat or solvents. It should have a sufficiently cohesive holding and elastic nature so that it can be removed from a surface without leaving a residue. PSAs are generally used in adhesive tapes and labels. An adhesive tape typically includes a substrate, i.e., a backing, to which the PSA is applied. Usually a primer is used to treat the surface of the backing to provide greater anchoring of the PSA. If the tape is stored in a rolled configuration the opposite surface of the backing is generally coated with a release coating, such as silicone, to allow unrolling of the tape.

Various types of PSAs are known. For example, PSA can be made from tackified natural or synthetic rubbers, ethylene-vinyl acetate copolymers, acrylics, vinyl acetate copolymers, silicones, and polymerized vinyl alkyl ethers.

Hot melt type PSAs are typically heated to a temperature sufficient to render the PSA sufficiently fluid so that it can be applied to a substrate.

Solution type PSA's are generally dissolved in a solvent to form a fluid which can be applied to a substrate. The solvent is thereafter evaporated to form the PSA coating.

Energy-curable formulations for making PSAs typically include unsaturated monomers or oligomers, especially acrylate type compounds. Such formulations also typically include a photoinitiator which is responsive to, for example, ultraviolet radiation (UV) for initiating polymerization. Such formulations are applied to a substrate as a fluid prepolymer, and are thereafter polymerized to form the PSA layer.

The properties of the PSA can be tailored by altering the type and/or composition percentage of the components in the formulation. However, it is not uncommon that improvement in one property of the PSA results in a detrimental change in another. For example, to increase the peel strength of the PSA a higher softening point tackifier can be used, or the content of di-or multi-functional oligomer resin can be increased. However, in each case, the PSA tack is reduced. What is needed is a method which can be used to improve the peel strength, while not incurring a corresponding detriment to the tack.

SUMMARY

An energy-curable polymer-forming composition is provided herein which includes an unsaturated oligomer resin and a compound of the general formula:

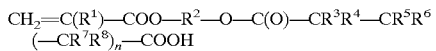

$$CH_2=C(R^1)-COO-R^2-O-C(O)-CR^3R^4-CR^5R^6(-CR^7R^8)_n-COOH$$

wherein $R^1$ is hydrogen or methyl, $R^2$ is a substituted or unsubstituted alkylene group having from 2 to about 6 carbon atoms, and $R^3$, $R^4$, $R^5$, $R^6$, $R^7$, and $R^8$ are independently selected from the group consisting of hydrogen and the other of said groups $R^3$ and $R^4$ is a straight or branched chain, saturated or unsaturated aliphatic, cycloaliphatic, or polycycloaliphatic groups possessing from 1 to about 20 carbon atoms, subject to the provision that at least one of groups $R^3$, $R^4$, $R^5$, $R^6$, $R^7$, and $R^8$ is, other than hydrogen, and n is 0 or 1.

The pressure sensitive adhesive derived from the composition described herein exhibits improved peel strength and tack.

DETAILED DESCRIPTION OF THE PREFERRED EMBODIMENT(S)

All quantities appearing hereafter shall be understood to be modified by the term "about" except in the Examples and where otherwise indicated.

The energy-curable PSA formulation of the present invention includes an unsaturated oligomer resin and a novel adhesion promoter discussed in detail below. The PSA formulation advantageously also includes a tackifier, chain extender and/or reactive diluent, and optionally a polymerization initiator and antioxidant. Various other optional additives can also be incorporated into the PSA formulation, such as plasticizers, fillers, colorants, fibers, glass or polymeric particles, electrically or thermally conducting particles, and other such materials known in the art.

A range of typical component percentages for energy-curable PSA formulations is given below in Table I.

TABLE I

| Component | (% by Weight) Broad Range | Preferred Range |
| --- | --- | --- |
| Oligomer Resin | from 10% to 70% | from 30% to 40% |
| Chain Extender | from 0% to 50% | from 20% to 30% |
| Reactive Diluent | from 0% to 50% | from 2% to 10% |
| Tackifier | from 5% to 50% | from 10% to 30% |
| Adhesion Promoter | from 0% to 50% | from 2% to 10% |
| Polymerization Initiator | from 0.1% to 20% | from 3% to 10% |
| Antioxidant | from 0% to 5% | from 0.5% to 2% |
| Polymerization Stabilizer | from 0.01% to 1% | from 0.05% to 0.2% |

Referring now more specifically to the individual components, the oligomers used in the energy-curable PSA formulation are liquid at room temperature without adding solvent thereto and contain at least one unsaturated double bond at terminals or side chains of the molecule.

These liquid oligomers can be synthesized by various, for example, methods such as:

(1) A condensation polymerization process by reacting a diol and a diacid or diester with a number average molecular weight of from about 500 g/mole to about 40,000 g/mole in a suitable organic solvent by a conventional solution polymerization, and then reacting the hydroxyl groups on the resulting polyester with an acrylic or methacrylic acid in the presence of a polymerization inhibitor and a catalyst to introduce olefinic unsaturated bonds into the resin;

(2) A condensation polymerization process by reacting a diamine and a diacid or diester with a number average molecular weight of from about 500 g/mole to about 40,000 g/mole, and then reacting the hydroxyl groups on the resulting polyamide with an acrylic or methacrylic acid in the presence of a polymerization inhibitor and a catalyst to introduce olefinic unsaturated bonds into the resin;

(3) A condensation polymerization process by reacting a diol and a diisocyanate with a number average molecular weight of from about 500 g/mole to about 40,000 g/mole, and then reacting the resulting compound (half urethane) with a hydroxyl terminated acrylic molecule to introduce olefinic unsaturated bonds into the resin;

(4) A condensation polymerization by reacting a polyether and a diisocyanate with excess isocyanate functionality having a number average molecular weight of from about 500 g/mole to about 40,000 g/mole, and then reacting the resulting compound (half urethane) with a hydroxyl terminated acrylic molecule in the presence of a polymerization inhibitor and a catalyst to introduce olefinic unsaturated bonds into the resin;

(5) A condensation polymerization by reacting a diol and diacid or diester with excess functionality and having a number average molecular weight of from about 500 g/mole to about 40,000 g/mole, and then reacting the resulting compound with an unsaturated monomer having an epoxy group in the presence of a polymerization inhibitor and a catalyst to introduce olefinic unsaturated bonds into the resin;

(6) A polymerization process by reacting a hydroxyl terminated polyether and a diisocyanate, diol, or dicarboxylic acid with a number average molecular weight of from about 500 g/mole to about 40,000 g/mole, and then reacting the resulting epoxy functional compound with a carboxylic acid pendent vinyl monomer in the presence of a polymerization inhibitor and a catalyst to introduce olefinic unsaturated bonds into the resin.

The polyester compounds referred to above may be produced from linear, branched, or cyclic aliphatic or aryl diols or diacids such as, for example, neopentane diol, hexamethylene diol, cyclohexane diol, phthalic acid, adipic acid, or the like. The diisocyanate compounds can be, for example, tolylene diisocyanate, isophorone diisocyanate, hexamethylene diisocyanate, or the like.

The hydroxyl terminated acrylic molecules can be, for example, 2-hydroxyethyl acrylate, 2-hydroxyethyl methacrylate, 2-hydroxypropyl acrylate, 2-hydroxypropyl methacrylate, or the like. The carboxyl functional acrylic monomerse include, for example, acrylic acid, methacrylic acid and the like.

The acrylic ester compound to be used can include, for example, methyl acrylate, methyl methacrylate, ethyl acrylate, ethyl methacrylate, butyl acrylate, butyl methacrylate, isobutyl acrylate, isobutyl methacrylate, octadecyl acrylate, octadecyl methacrylate, 2-ethylhexyl acrylate, 2-ethylhexyl methacrylate, and the like. It is preferable that such an acrylic ester compound is present in the main chain of the oligomer in an amount of 5% by weight or more.

The monomer having a carboxyl group can include, for example, acrylic acid, methacrylic acid, and the like. The monomer having an epoxy group can include, for example, glycidyl acrylate, glycidyl methacrylate, etc. The monomer having a hydroxyl group includes, for example, 2-hydroxyethyl acrylate, 2-hydroxyethyl methacrylate, 2-hydroxypropyl acrylate, 2-hydroxypropyl methacrylate, etc. Further, the monomer having an amino group can include, for example, dimethylaminoethyl acrylate, dimethylaminoethyl methacrylate, diethylaminoethyl acrylate, diethylaminoethyl methacrylate, etc.

Suitable oligomers for use in the PSA formulation can be made by reacting lactone-acrylate adducts with polycarboxylic polyanhydrides in accordance with the method described in U.S. Pat. No. 5,912,381 to Narayan et al., which is herein incorporated by reference in its entirety. Preferred oligomers are urethane acrylate oligomers. An especially preferred oligomer resin for use in the PSA formulation herein is a difunctional aromatic urethane acrylate having a weight average molecular weight of from about 8,500 to about 30,000, preferably 16,000 to 18,000, which is available from Henkel Corporation under the designation RCC 13-572.

As used herein the term "tackifier" refers to any material which is useful to impart tack to the adhesive composition. Tack is defined by ASTM D-1878-61T as the property of a material which enables it to form a bond of measurable strength immediately on contact with another surface. Generally, tackifiers are useful in energy curable PSA formulations in concentrations ranging from 0% to about 50% by weight of the formulation, preferably from about 10% to 30% by weight.

Tackifiers for use in the present formulation can include natural and synthetic terpenes, phenol modified terpenes, tall oil, gum rosin, wood rosin, hydrocarbon resins such as polyvinyl cyclohexane and poly (t-butyl styrene), and rosin esters such as glycerol esters of rosin and pentaerythritol esters of rosin. Suitable tackifiers for use in the PSA formulation include commercially available Norsolene hydrocarbon resin.

Chain extenders can be incorporated into the PSA formulation to extend the chain length of the oligomer. Chain extenders build linear structures between crosslinking points. Preferred chain extenders for use in the PSA formulation of the present invention include nonyl phenol ethoxylate monoacrylate (available from Henkel Corporation under the designation PH 4003), 2-phenoxy ethyl acrylate (available from Henkel Corporation under the designation PH 4035), phenol ethoxylate monoacrylate (available from Henkel Corporation under the designation PH 4039), and propoxylated nonylphenol acrylate, (available from Henkel Corporation under the designation RCC 12-960).

Reactive diluents are used to lower the viscosity of the PSA formulation to facilitate application of the formulation to a substrate at room temperature. Reactive diluents include a wide variety of free-radically polymerizable monomers such as: mono-acrylates and methacrylates such as methyl acrylate, methyl methacrylate, ethyl acrylate, isopropyl methacrylate, isooctyl acrylate, isobornyl acrylate, isobornyl methacrylate, acrylic, n-hexyl acrylate, stearyl acrylate, allyl acrylate, tetrahydrofurfuryl(meth) acrylate, 2(2-ethoxyethoxy)ethyl acrylate, 2-phenoxyethyl acrylate, ethoxylated nonyl phenol acrylate, copolymerizable mixtures of acrylated monomers such as those of U.S. Pat. No. 4,652,274, and acrylated oligomers such as those of U.S. Pat. No. 4,642,126, both of which are incorporated herein by reference. A preferred reactive diluent is monomethoxy tripropylene glycol monoacrylate, available from Henkel Corporation under the designation Photomer® 8061. Also useful is a reactive amine/tripropylene glycol diacrylate adduct available from Henkel Corporation under the designation RCC 12-967.

The PSA formulation of the present invention includes a novel adhesion promoter which includes a compound having the general formula:

$$CH_2=C(R^1)-COO-R^2-O-C(O)-CR^3R^4-CR^5R^6(-CR^7R^8)_n-COOH \quad (I)$$

wherein $R^1$ is hydrogen or methyl, $R^2$ is a substituted or unsubstituted alkylene groups having from 2 to about 6 carbon atoms, and $R^3$, $R^4$, $R^5$, $R^6$, $R^7$, and $R^8$ are independently selected from the group consisting of hydrogen and straight or branched chain, saturated or unsaturated aliphatic, cycloaliphatic or polycycloaliphatic groups possessing from 1 to about 20 carbon atoms, subject to the provision that at least one of groups $R^3$, $R^4$, $R^5$, $R^6$, $R^7$, and $R^8$ is other than hydrogen, and n is 0 or 1. In one preferred embodiment, at least one of $R^3$, $R^4$, $R^5$, $R^6$, $R^7$, or $R^8$ is an unsaturated aliphatic group. Octenyl and dodecenyl are particularly preferred examples of suitable substituents.

Suitable adhesion promoters include, for example, the compounds having the following formulas:

$$CH_2=CH-COO-CH_2CH_2-O-C(O)-CH_2C(C_8H_{15})H-COOH \quad (II)$$

$$CH_2=C(CH_3)-COO-CH_2CH_2-O-C(O)-CH_2C(C_8H_{15})H-COOH \quad (III)$$

$$CH_2=CH-COO-CH_2C(CH_3)H-O-C(O)-CH_2C(C_8H_{15})H-COOH \quad (IV)$$

$$CH_2=C(CH_3)-COO-CH_2C(CH_3)H-O-C(O)-CH_2C(C_8H_{15})H-COOH \quad (V)$$

$$CH_2=CH-COO-CH_2CH_2-O-C(O)-CH_2C(C_{12}H_{23})H-COOH \quad (VI)$$

$$CH_2=C(CH_3)-COO-CH_2CH_2-O-C(O)-CH_2C(C_{12}H_{23})H-COOH \quad (VII)$$

$$CH_2=CH-COO-CH_2C(CH_3)H-O-C(O)-CH_2C(C_{12}H_{23})H-COOH \quad (VIII)$$

$$CH_2=C(CH_3)-COO-CH_2C(CH_3)H-O-C(O)-CH_2C(C_{12}H_{23})H-COOH \quad (IX)$$

The most preferred adhesion promoters include the octenyl-mono{1-methyl-2-[(2-methyl-1-oxo-2-propenyl)oxy]-1-methyl-ethyl}ester of butanedioic acid (Compound V, above); dodecenyl mono{1-methyl-2-[(2-methyl-1-oxo-2-propenyl)oxy]-1-methyl-ethyl}ester of butanedioic acid (Compound IX, above); the octenyl-mono{2-[(2-methyl-1-oxo-2-propenyl)oxy]ethyl}ester of butanedioic acid (Compound III, above); and the dodecenyl mono{2-[(2-methyl-1-oxo-2-propenyl)oxy]ethyl}ester of butanedioic acid (Compound VII, above).

The adhesion promoter of the present invention can be synthesized by reacting in a conventional manner a hydroxy alkyl ester of (meth)acrylic acid with, for example, an alkyl-, alkenyl-, or alkynyl-substituted cyclic anhydride such as a substituted succinic anhydride, substituted glutaric anhydride, or the like. Thus, the hydroxyalkyl ester of (meth) acrylic acid has the formula:

$$CH_2=C(R^1)-COO-R^2-OH$$

wherein $R^1$ is hydrogen or methyl, and $R^2$ is a substituted or unsubstituted alkylene group having from 2 to about 6 carbon atoms. Preferred unsubstituted alkylene groups include, for example, $-CH_2CH_2-$ and $-CH_2CH_2CH_2-$. A suitable methyl substituted alkylene group can include, for example, $-CH_2C(CH_3)H-$. Suitable hydroxy alkyl (meth) acrylate esters include, for example, hydroxy ethyl acrylate, hydroxyethyl methacrylate, hydroxypropyl acrylate, and hydroxypropyl methacrylate. Suitable alkyl, alkenyl and alkynyl-substituted anhydrides are known in the art and commercially available.

The adhesion promoter of the present invention advantageously improves both peel strength and tack. Table II below sets forth a comparison of PSAs prepared from formulations including adhesion promoters in accordance with formula I above as opposed to PSAs without adhesion promoter or with adhesion promoters lacking the aliphatic group of $R^3$ or $R^4$. In Table II, Compound A has the formula $$CH_2=CH-COO-CH_2CH_2-O-C(O)-CH_2CH_2-COOH$$

and Compound B has the formula $$CH_2=C(CH_3)-COO-CH_2CH_2-O-C(O)-CH_2CH_2-COOH$$

and, therefore, neither Compound A nor Compound B falls within the scope of the present invention. Compounds II, III, and VII are respectively in accordance with the formulas II, III, and VII given above.

TABLE II (Characteristics of PSAs containing different adhesion promoters)

| Adhesion Promoter | Peel Strength (g/in.) | Loop Tack (g/in$^2$) |
| --- | --- | --- |
| None | 800 | 900 |
| Compound A | 750–800 | 900 |
| Compound B | 800 | 750–800 |
| Compound II | 950 | 1150 |
| Compound III | 1350 | 1500 |
| Compound VII | 1250 | 1400 |

As can be seen from Table II, PSAs containing Compounds II, III, and VII of the present invention are characterized by at least an 18% greater peel strength and 27% greater loop tack than PSAs containing no adhesion promoter or Compounds A or B, above.

Curing of the PSA formulation is accomplished by exposure to a suitable energy source such as, for example, heat, ultraviolet (UV) radiation, or electron beam (EB) radiation. If EB radiation is used the PSA formulation does not need a polymerization initiator. However, if UV radiation or heat curing are contemplated a suitable photoinitiator or thermal initiator is required.

Photoinitiators suitable for use herein include 2-hydroxy-2-methyl-1-phenyl-1-propanone, benzildimethyl ketal, 2,2-diethoxy-1,2-diphenylethanone, 1-hydroxy-cyclohexyl-phenylketone, 1-(4-isopropylphenyl)-2-hydroxy-2-methyl-propan-1-one, 1-[4-(2-hydroxyethoxy)phenyl]-2-hydroxy-2-methyl-propan-1-one, 2-methyl-1-[4-(methylthio)phenyl]-2-morpholino-propan-1-one, 2-benzyl-2-dimethylamino-1-(4-morpholinophenyl)-butan-1-one, 3,6-bis(2-methyl-2-morpholino-propanonyl)-9-butyl-carbazole, 4,4'-bis(dimethylamino)benzophenone, 2-chlorothioxanthone, 4-chlorothioxanthone, 2-isopropylthioxanthone, 4-isopropylthioxanthone, 2,4-dimethylthioxanthone, 2,4-diethylthioxanthone, 4-benzoyl-N,N-dimethyl-N-[2-(1-oxo-2-propenyl)oxy] ethylbenzenemethanaminium chloride, methyldiethanolamine, triethanolamine, ethyl 4-(dimethylamino)benzoate, 2-n-butoxyethyl 4-(dimethylamino)benzoate and combinations thereof.

Of the above listed photoinitiators the most preferred are 2-hydroxy-2-methyl-1-phenyl-1-propanone (available from Ciba-Geigy under the designation Darocur 1173) and 2-benzyl-2-dimethylamino-1-(4-morpholinophenyl)-butan-1-one (available from Ciba-Geigy under the designation Irgacure 369).

Thermal initiators include peroxides, hydroperoxides, peresters, and diazo compounds such as, for example, dibenzoyl peroxide, acetyl peroxide, benzoyl hydroperoxide, di-tert-butyl peroxide, tert-butyl hydroperoxide, tert-butyl perbenzoate, and the like.

A suitable antioxidant for use in the present invention is tetrakis [methylene (3,5-di-tert-butyl-4-hydroxyhydrocinnamate] methane, which is available from Ciba-Geigy Corporation under the designation Irganox 1010.

A polymerization stabilizer is preferably added to prevent premature polymerization of the formulation prior to the intended curing step. Methylethylhydroquinone (MEHQ) is a suitable stabilizer.

The PSA formulation is made by mixing the components listed above in a suitable vessel.

The prepared formulation is in a fluid condition when uncured, and is applied by spraying, brushing, wiping (or other suitable method) to a suitable substrate, for example a backing strip for an adhesive tape or label. PSAs are used, for example, in masking tape, packaging tape, sealing tapes, transparent tapes, medical tapes, self-stick removable notes, and self-sealing envelopes and packages, as well as digital video disks. The substrates to which the PSA can be applied include paper, flexible polymeric film, rigid plastics, metal (e.g., metal foils or sheets), ceramics, glass, wood, and the like.

In the method of coating a substrate according to the invention, the PSA formulation, optionally containing a photoinitiator, is applied to the surface of the substrate and subsequently exposed to a radiation source until an adherent dry polymerized film is formed on the substrate. Sources of radiant energy appropriate for initiating cure of the formulations have been described extensively in the literature and are well known to those skilled in the art. These include various sources of particulate and non-particulate radiation producing wavelengths generally less than 700 nanometers. Especially useful is actinic radiation in the 180–440 nm range which can be conveniently obtained by use of one of several commercially available ultra-violet sources specifically intended for this purpose. These include low, medium and high pressure mercury vapor lamps, He—Cd and Ar lasers, xenon arc lamps, etc. Photoinitiator systems having a corresponding sensitivity to light in this wave band are normally incorporated into the formulation and upon irradiation lead to the formation of reactive species capable of initiating free radical polymerization. Similarly, free radical polymerization may be induced by exposure of the formulation to an electron beam without the use of a photoinitiator. Equipment capable of generating a curtain of electrons with energies between 150 and 300 KeV is particularly suitable for this purpose and its use is well documented in the literature.

Particularly preferred sources of radiation emit electromagnetic radiation predominantly in the ultra-violet band. When such a source is used, the polymerizable composition preferably contains a photoinitiator susceptible to ultraviolet radiation.

The amount of radiation necessary to cure the composition will of course depend on the angle of exposure to the radiation, the thickness of the coating to be applied, and the amount of polymerizable groups in the coating composition as well as the presence or absence of a free radical initiating catalyst. For any given composition, experimentation to determine the amount of radiation sensitive pi bonds not cured following exposure to the radiation source is the best method of determining the amount and duration of the radiation required. Typically, an ultra-violet source with a wavelength between 20 and 420 nm (e.g. a filtered mercury arc lamp is directed at coated surfaces carried on a conveyor system which provides a rate of passage past the ultra-violet source appropriate for the radiation absorption profile of the composition (which profile is influenced by the degree of cure desired, the thickness of the coating to be cured, and the rate of polymerization of the composition).

The quality of the resulting PSA coating is determined by properties such as "peel adhesion", "quick stick," "rolling ball tack", and "shear adhesion".

Peel adhesion is the force required to remove a pressure sensitive tape from a panel or its own backing at a specified angle and speed. Peel adhesion can be measured in accordance with the Pressure Sensitive Tape Council PSTC-1 test standard.

Quick stick is that property of a pressure sensitive tape which causes the tape to adhere to a surface instantly, using no external pressure to secure more thorough contact. In accordance with standardized test PSTC-5, quick stick is measured as the force resisting peeling of a tape at 90° angle from a standard surface upon which it has bene applied under no pressure other than the weight of the tape itself.

The rolling ball tack test PSTC-6 measures the tack of adhesive tape where the adhesion is insufficient to give a reading using standard peel adhesion method.

Shear adhesion is defined as the force required to pull the pressure sensitive tape from a standard flat surface in a direction parallel to the surface to which it has been affixed with a definite pressure. In accordance with standard test PSTC-7 shear adhesion is measured in terms of the time required to pull a standard area of tape from a test panel under a standard load, or in terms of the distance the tape has been displaced in a given time on a test panel under a standard load.

The following Examples below are presented for the purpose of illustrating various aspects of the present invention. The following Comparative Example A illustrates a PSA formulation which does not include the adhesion promoter of the present invention.

EXAMPLE 1

Synthesis of Urethane Acryalate Oligomer

A quantity of 0.1 moles of isocyanate terminated prepolymer and 0.1 ml of dibutyltin laurate were charged to a 500 ml glass kettle. The mixture was heated at 70° C. and air was purged through the reaction mixture and a solution of diol (0.05 moles) was added dropwise while the mixture was stirred at 200 RPM. After a two hour reaction, hydroxyethyl acrylate (0.1 moles) was added to cap the residual isocyanate and the temperature of the kettle was increased to 77° C. After another two hours, a sample was withdrawn for analysis. The remainder was transferred to a bottle and stored in darkness.

EXAMPLE 2

Synthesis of Adhesion Promoter

A quantity of 61.43 grams of hydroxyethyl methacrylate (HEMA) was mixed with 0.11 g methylethyl hydroquinone (MEHQ) and 0.375 g triphenyl phosphine (TPP). To this mixture 94.50 g n-octenyl succinic anhydride was added dropwise over a 10 minute period. The temperature of the mixture was elevated to 88° C. during the addition. After the addition the temperature of the mixture was elevated to 100° C. Air was sparged into the reaction mixture during the whole course of the reaction. A quantity of 150.3 g of total product was recovered. The product has a viscosity of 200 cps (Brookfield, spindle #3) and a density of 1.03 g/ml.

EXAMPLE 3

Synthesis of Adhesion Promoter

A quantity of 68.00 grams of hydroxypropyl methacrylate was mixed with 0.11 g MEHQ and 0.375 g TPP. To this mixture 94.50 g n-octenyl succinic anhydride was added dropwise over a 10 minute period. The temperature of the mixture was elevated to 88° C. during the addition. After the addition the temperature of the mixture was elevated to 100° C. Air was sparged into the reaction mixture during the whole course of the reaction. A quantity of 161.0 g of total product was recovered. The product has a viscosity of 300 cps (Brooldield, spindle #3) and a density of 1.03 g/ml.

EXAMPLE 4

Synthesis of Adhesion Promoter

A quantity of 36 grams of hydroxypropyl methacrylate was mixed with 0.072 g MEHQ and 0.26 g TPP. To this mixture 66.5 g n-dodecenyl succinic anhydride was added dropwise over a 10 minute period. The temperature of the mixture was elevated to 88° C. during the addition. After the addition the temperature of the mixture was elevated to 100° C. Air was sparged into the reaction mixture during the whole course of the reaction.

EXAMPLE 5

A urethane oligomer resin was prepared which included: adipic acid/neo-pentylglycol polyester diol/isophorone diisocyanate/hydroxyethyl acrylate.

The urethane oligomer was prepared by charging adipic acid and neopentyl glycol polyester diol to a flask, and sparging with $N_2$ while heating up to 65° C. Isophorone diisocyanate (IDPI) was then added over a 15 minute period. The temperature of the reaction was elevated to 85° C. for 1 hour. The temperature was then lowered to 70° C. and 2-hydroxyethyl acrylate (HEA) was added over a 10 minute period. The temperature of the reaction was then elevated to 90° C. for 1 hour 45 minutes. Then one reaction mixture was cooled to 80° C. and then removed from the flask and stored. The resulting resin was a clear, light yellow tinted viscous material having a viscosity of 64,906 cps (Brookfleld DVIII viscometer #34 spindle, 0.5 rpm at 60° C.). The weight average molecular weight ($M_w$) of the resin was 15,500 and the ratio ($M_w/M_n$) of the weight average molecular weight to the number average molecular weight ($M_n$) was 3.7.

The urethane oligomer resin produced in this Example is hereinafter designated as Urethane resin A.

EXAMPLE 6

A PSA formulation was prepared by mixing the following components, wherein "phr" stands for parts by weight per 100 parts by weight of polymer in the composition. Compound V, as indicated above, is the octenyl-mono{1-methyl-2-[(2-methyl-1-oxo-2-propenyl)oxy]-1-methyl-ethyl}ester of butanedioic acid.

| Component | Parts by Weight |
|---|---|
| Urethane resin A (Example 5) | 34 |
| Reactive Diluent (Photomer 8061) | 6 |
| Adhesion Promoter (Compound V) | 6 |
| Chain Extender (PH 4003) | 23 |
| Tackifier (Norsolene S-115) | 20 |
| Stabilizer (MEHQ) | 0.1 phr |
| Antioxidant (Irganox 1010) | 1 |
| Photoinitiator (Darocur 1173) | 10 |

The PSA formulation herein was then applied to a polymer film and cured using a F300SD UV bulb at 25 ft./min. to fabricate a PSA tape. The tape was then tested for peel strength using PSTC-1, for loop tack using PSTC-5, and for shear strength using PSTC-7 standard test procedures.

The cured PSA exhibited the following characteristics:

| | |
|---|---|
| 180 Peel Strength | 1370 g/in |
| Loop tack | 1420 g/in$^2$ |
| Shear | 1780 min. |

EXAMPLE 7

A PSA formulation was prepared by mixing the following components.

| Component | Parts by weight |
|---|---|
| Urethane Resin A | 37 |
| Photomer 8061 | 6.5 |
| Compound V | 6.5 |
| PH 4003 | 24.8 |
| Norsolene S-115 | 21.8 |
| MEHQ | 0.1 phr |
| Irganox 1010 | 1.2 |
| Darocur 1173 | 2.2 |

The formulation was applied to a polymer film and cured in the same manner as in Example 6. The PSA tape was thereafter tested in the same manner as in Example 6. The cured PSA exhibited the following characteristics:

| | |
|---|---|
| 180° Peel Strength | 1540 g/in |
| Loop tack | 1080 g/in$^2$ |
| Shear | >10,000 min. |

EXAMPLE 8

A PSA formulation was prepared by mixing the following components.

| Component | Parts by weight |
|---|---|
| Urethane Resin A | 35.5 |
| Photomer 8061 | 6.3 |
| Compound V | 6.3 |
| PH 4003 | 23.8 |
| Norsolene S-115 | 20.8 |

-continued

| Component | Parts by weight |
| --- | --- |
| MEHQ | 0.1 phr |
| Irganox 1010 | 1.0 |
| Darocur 1173 | 6.3 |

The formulation was applied to a polymer film and cured in the same manner as in Example 6. The PSA tape was thereafter tested in the same manner as in Example 6. The cured PSA exhibited the following characteristics:

| | |
| --- | --- |
| 180° Peel Strength | 1,400 g/in |
| Loop tack | 1,440 g/in$^2$ |
| Shear | 5,660 min. |

COMPARATIVE EXAMPLE A

A PSA formulation was prepared by mixing the following components, which do not include an adhesion promoter.

| Component | Parts by weight |
| --- | --- |
| Urethane Resin A | 34 |
| Photomer 8061 | 6 |
| PH 4003 | 29 |
| Norsolene S-115 | 20 |
| MEHQ | 0.1 phr |
| Irganox 1010 | 1 |
| Darocur 1173 | 10 |

The formulation was applied to a polymer film, cured and tested in the same manner as Example 6. The cured PSA exhibited the following characteristics:

| | |
| --- | --- |
| 180° Peel Strength | 742 g/in |
| Loop tack | 863 g/in$^2$ |
| Shear | 5,000 min. |

As can be seen from Table III below, which summarizes the test results from Examples 6, 7, 8 and the present Comparative Example A, incorporation of the adhesion promoter of the present invention into the PSA formulation significantly improves the characteristics of the cured PSA, especially with regard to 180° peel strength and loop tack.

TABLE III

| Example | Peel Strength (g/in) | Loop tack (g/in$^2$) | Shear (min) |
| --- | --- | --- | --- |
| 6 | 1,370 | 1,420 | 1,780 |
| 7 | 1,540 | 1,080 | >10,000 |
| 8 | 1,400 | 1,440 | 5,660 |
| Comp. Ex. A | 742 | 863 | 5,000 |

COMPARATIVE EXAMPLE B

A low strength masking tape commercially available from Manco Co. was tested for 180° peel strength and loop tack in accordance with the testing procedures of Example 6 above. The masking tape exhibited a peel strength of 830 g/in. and a loop tack of 440 g/in$^2$.

COMPARATIVE EXAMPLE C

A high strength packaging tape commercially available from 3M Co. under the designation Scotch® 3750 was tested for 180° peel strength and loop tack in accordance with the testing procedures of Example 6 above. The packaging tape exhibited a peel strength of 1090 g/in. and a loop tack of 1250 g/in$^2$. As can be seen, the PSA produced from the formulation of the present invention exhibited a higher peel strength and loop tack than the commercially available product.

While the above description contains many specifics, these specifics should not be construed as limitations on the scope of the invention, but merely as exemplifications of preferred embodiments thereof. Those skilled in the art will envision many other possible variations within the scope and spirit of the claims appended hereto.

What is claimed is:

1. An energy-curable polymer-forming composition which comprises:

a) an unsaturated oligomer liquid resin; and b) an adhesion promoter having the formula

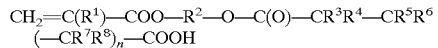

wherein $R^1$ is hydrogen or methyl, $R^2$ is a substituted or unsubstituted alkylene group having from 2 to about 6 carbon atoms, and $R^3$, $R^4$, $R^5$, $R^6$, $R^7$, and $R^8$ are independently selected from the group consisting of hydrogen and straight or branched chain, saturated or unsaturated aliphatic, cycloaliphatic, or polycycloaliphatic groups possessing from 1 to about 20 carbon atoms, subject to the provision that at least one of groups $R^3$, $R^4$, $R^5$, $R^6$, $R^7$, or $R^8$ is other than hydrogen and n is 0 or 1, wherein the composition additionally comprises a tackifier selected from the group consisting of natural terpenes, synthetic terpenes, phenol modified terpenes, tall oil, gum rosin, wood rosin, glycerol esters of rosin, pentaerythritol esters of rosin, polyvinyl cyclohexane, and poly(t-butyl styrene).

2. The composition of claim 1 wherein $R^1$ is methyl.

3. The composition of claim 1 wherein $R^2$ is —CH$_2$CH$_2$—.

4. The composition of claim 1 wherein $R^2$ is —CH$_2$C(CH$_3$)H—.

5. An energy-curable polymer-forming composition which comprises:

a) an unsaturated oligomer liquid resin; and b) an adhesion promoter having the formula

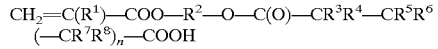

wherein $R^1$ is hydrogen or methyl, $R^2$ is a substituted or unsubstituted alkylene group having from 2 to about 6 carbon atoms, and $R^3$, $R^4$, $R^5$, $R^6$, $R^7$, and $R^8$ are independently selected from the group consisting of hydrogen and straight or branched chain, saturated or unsaturated aliphatic, cycloaliphatic, or polycycloaliphatic groups possessing from 1 to about 20 carbon atoms, subject to the provision that at least one of groups $R^3$, $R^4$, $R^5$, $R^6$, $R^7$, or $R^8$ is —C$_8$H$_{15}$ and n is 0 or 1.

6. The composition of claim 5 wherein $R^1$ is hydrogen and $R^2$ is —CH$_2$CH$_2$—.

7. The composition of claim 5 wherein $R^1$ is hydrogen and $R^2$ is —CH$_2$C(CH$_3$)H—.

8. The composition of claim 5 wherein $R^1$ is methyl and $R^2$ is —CH$_2$CH$_2$—.

9. The composition of claim 5 wherein $R^1$ is methyl and $R^2$ is —CH$_2$C(CH$_3$)H—.

10. An energy-curable polymer-forming composition which comprises:

a) an unsaturated oligomer liquid resin; and b) an adhesion promoter having the formula

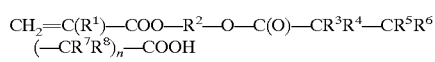

wherein $R^1$ is hydrogen or methyl, $R^2$ is a substituted or unsubstituted alkylene group having from 2 to about 6 carbon atoms, and $R^3$, $R^4$, $R^5$, $R^6$, $R^7$, and $R^8$ are independently selected from the group consisting of hydrogen and straight or branched chain, saturated or unsaturated aliphatic, cycloaliphatic, or polycycloaliphatic groups possessing from 1 to about 20 carbon atoms, subject to the provision that at least one of groups $R^3$, $R^4$, $R^5$, $R^6$, $R^7$, and $R^8$ is —C$_{12}$H$_{23}$ and n is 0 or 1.

11. The composition of claim 10 wherein $R^1$ is hydrogen and $R^2$ is —CH$_2$CH$_2$—.

12. The composition of claim 10 wherein $R^1$ is hydrogen and $R^2$ is —CH$_2$C(CH$_3$)H—.

13. The composition of claim 10 wherein $R^1$ is methyl and $R^2$ is —CH$_2$CH$_2$—.

14. The composition of claim 10 wherein $R^1$ is methyl and $R^2$ is —CH$_2$C(CH$_3$)H—.

15. The composition of claim 1 wherein the oligomer resin is a diacrylate functional aromatic urethane.

16. The composition of claim 1 additionally comprising a polymerization initiator.

17. The composition of claim 16 wherein the polymerization initiator is a photoinitiator selected from the group consisting of 2-hydroxy-2-methyl-1-phenyl-1-propanone, benzildimethyl ketal, 2,2-diethoxy-1,2-diphenylethanone, 1-hydroxy-cyclohexyl-phenyl ketone, 1-(4-isopropylphenyl)-2-hydroxy-2-methyl-propan-1-one, 1-[4-(2-hydroxyethoxy)phenyl]-2-hydroxy-2-methyl-propan-1-one, 2-methyl-1-[4-(methylthio)phenyl]-2-morpholino-propan-1-one, 2-benzyl-2-dimethylamino-1-(4-morpholinophenyl)-butan-1-one, 3,6-bis(2-methyl-2-morpholino-propanonyl)-9-butyl-carbazole, 4,4'-bis (dimethylamino)benzophenone, 2-chlorothioxanthone, 4-chlorothioxanthone, 2-isopropylthioxanthone, 4-isopropylthioxanthone, 2,4-dimethylthioxanthone, 2,4-diethylthioxanthone, 4-benzoyl-N,N-dimethyl-N-[2-(1-oxo-2-propenyl)oxy]ethylbenzenemethanaminium chloride, methyldiethanolamine, triethanolamine, ethyl 4-(dimethylamino)benzoate, 2-n-butoxyethyl-4-(dimethylamino)benzoate and combinations thereof.

18. The composition of claim 16 wherein the polymerization initiator is a photoinitiator selected from the group consisting of 2-hydroxy-2-methyl-1-phenyl-1-propanone and 2-benzyl-2-dimethylamino-1-(4-morpholinophenyl)-butan-1-one.

19. An energy-curable polymer-forming composition which comprises:

a) an unsaturated oligomer liquid resin; and b) an adhesion promoter having the formula

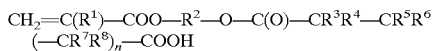

wherein $R^1$ is hydrogen or methyl, $R^2$ is a substituted or unsubstituted alkylene group having from 2 to about 6 carbon atoms, and $R^3$, $R^4$, $R^5$, $R^6$, $R^7$, and $R^8$ are independently selected from the group consisting of hydrogen and straight or branched chain, saturated or unsaturated aliphatic, cycloaliphatic, or polycycloaliphatic groups possessing from 1 to about 20 carbon atoms, subject to the provision that at least one of groups $R^3$, $R^4$, $R^5$, $R^6$, $R^7$ or $R^8$ is other than hydrogen and n is 0 or 1, wherein the composition additionally comprises a tackifier wherein the tackifier is a hydrocarbon resin.

* * * * *